United States Patent [19]

Van der Knaap

[11] Patent Number: Plant 5,825

[45] Date of Patent: Dec. 9, 1986

[54] KALANCHOE PLANT NAMED STROMBOLI

[75] Inventor: Jacques C. M. Van der Knaap, De Lier, Netherlands

[73] Assignee: Ball Panam Plant Company, Parris, Fla.

[21] Appl. No.: 706,594

[22] Filed: Feb. 28, 1985

[51] Int. Cl.[4] ..... A01H 5/00

[52] U.S. Cl. ..... Plt./68

[58] Field of Search ..... Plt./68

*Primary Examiner*—R. E. Bagwill

*Attorney, Agent, or Firm*—Schwartz, Jeffery, Schwaab, Mack, Blumenthal & Evans

[57] ABSTRACT

A Kalanchoe plant named Stromboli, having red flower color, strong growth and freely branching habit, high floriferousness, relatively short crop time, and adaptability for production in pots of varying diameter.

1 Drawing Figure

1

The present invention relates to a new and distinctive cultivar of Kalanchoe, plant, botanically known as Kalanchoe, and referred to by the cultivar name Stromboli.

The new cultivar was referred to during the breeding and selection process by the designation Sonate×Wega and is a product of a planned breeding program. The basic objective of the breeding program was to create a new Kalanchoe cultivar having a short crop time, good foliage, good color, and good keeping qualities for a year around Kalanchoe.

The new cultivar was originated by Applicant from a cross made in a controlled breeding program in De Lier, Netherlands. The female, or seed parent was an unpatented cultivar named Sonate. The male, or pollen parent was a cultivar named Wega, similarly unpatented.

Stromboli was discovered and selected by me as a flowering plant within the progeny of the stated cross in a controlled environment in De Lier, Netherlands. Asexual reproduction of the new cultivar by stem cuttings, as performed by me at De Lier, Netherlands, has demonstrated that the combination of characteristics as herein disclosed for the new cultivar are firmly fixed and are retained through successive generations of asexual reproduction.

Stromboli has not been observed under all possible environmental conditions. The phenotype may vary significantly with variations in environment such as temperature, light intensity and day length. The following observations, measurements and values describe the new cultivar as grown in De Lier, Netherlands, under greenhouse conditions which closely approximate those generally used in commercial practice.

The following traits have been repeatedly observed and are determined to be basic characteristics of Stromboli, which in combination distinguish this Kalanchoe as a new and distinct cultivar:

1. Excellent red flower color.
2. Strong growth habit compared to other cultivars of this type.
3. Freely branching, with shoots formed at every node.
4. Suitable for production in 10 cm. pots.
5. Highly floriferous, with numerous flowers formed at every shoot.
6. To reduce peduncle elongation after flower initiation, plants must be treated with Alar or B9.

2

Stromboli is most similar to the paternal parent Wega, being principally distinguished from Wega by its red flower color, keeping qualities, vigor, and shorter crop period.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values are taken under natural light conditions at approximately 12:00 p.m. noon in De Lier, Netherlands.

Botanical classification: Kalanchoe, cv. Stromboli.

Parentage:

*Male parent.*—Wega.

*Female parent.*—Sonate.

Propagation:

(A) *Type cutting.*—Shoot cuttings.

(B) *Time to root.*—12 days at 21° C. summer, and 17 days winter.

(C) *Rooting habit.*—Many large, thick roots.

Plant description:

(A) *Form.*—Upright, medium-sized. Growing and scheduling practices can produce medium-sized or large plants.

(B) *Habit of growth.*—High growth rate for this type of plant. Generally shoots are formed at every node.

(C) *Foliage description.*—Leaves simple, opposite, general symmetrical. (1) Size: Average, full grown leaf of a flowering plant in a 11 cm. pot is 125 mm. long and 84 mm. wide. (2) Shape: Eclipse, apex acute to obtuse, base acute. (3) Texture: Glaborous, coriaceous, succulent. (4) Margin: Crenate. (5) Color: Young foliage, top side 147A, under side 147B. Mature foliage, top side 147A, under side 147B.

Flowering description:

(A) *Flowering habits.*—Inflorescence of each shoot is formed by dichotomous branching, starting with opening of terminal flower at main axis, followed by terminal flowers of the side branches of the inforescence. Opening of new buds will continue for nine weeks or more. Individual flowers last three weeks or more after opening.

(B) *Natural flowering season.*—November. Flowering time under controlled day length at 25° C. in summer is 10 weeks; in winter at 20° C., 12 weeks. Flowering time depends on temperature, light intensity and other growing conditions.

(C) *Flower buds.*—Oblong, developing to tubular as petals mature; sheathed with four green sepals; corolla at maturity about 16 mm. (1) Size; 17 mm. (2) Shape: Oblong. (3) Rate of Opening: Normal.

(D) *Flowers borne.*—Compound dichasial cyme on fairly strong peduncles. Peduncle length up to 5 mm., depending on growing conditions and applications of B9 or Alar.

(E) *Quantity of flowers.*—Very floriferous, with new buds continuing to develop.

(F) *Petals.*—(1) Shape: Nearly round, apex cuspidate. (2) Color: Top side when opening, 44B, fading to 44C; under side, 43D. (3) Number and size of petals: Four, united in corolla; petals, 6 mm, in diameter, total diameter.

(G) *Reproductive organs.*—(1) Stamens: Eight in number. (a) Anther shape: Flat, Elliptical. (b) Filament color: Yellow. (c) Pollen color: Yellow. (2) Pistels (a) Stigma shape: Flat, crystalline. (b) Style color: Greenish-white. (c) Ovaries, Four-celled, 7 mm. long, green.

Disease resistance: No known Kalanchoe diseases observed to date.

General observations: Stromboli is particularly noted for its bright red flower color, strong and freely branching habit, average 11 weeks flowering response, and its adaptability to production in 10–12 cm. pots.

I claim:

1. A new and distinct cultivar of Kalanchoe named Stromboli, as described and illustrated, and particularly characterized by its red flower color, strong growth and freely branching habit, high floriferousness, relatively short crop time, and adaptability for production in pots of varying diameter.

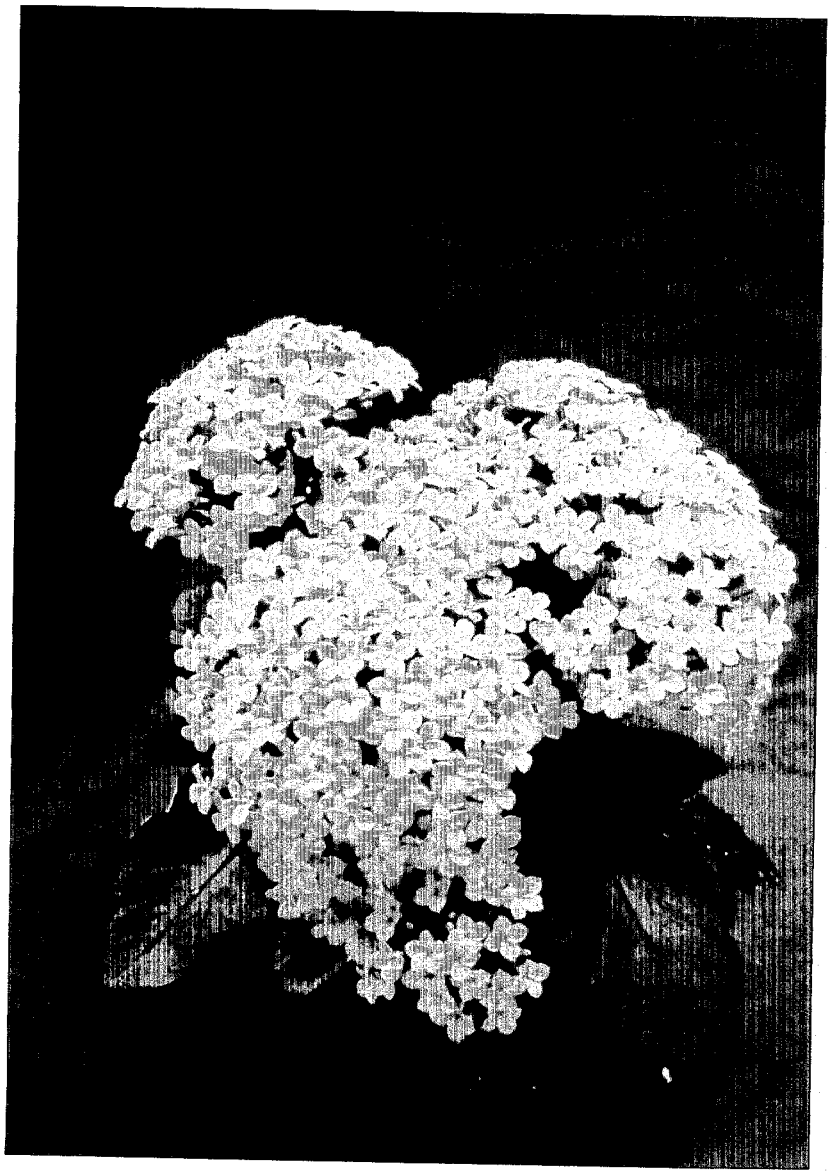

* * * * *